United States Patent
Wloka et al.

(10) Patent No.: US 8,329,951 B2
(45) Date of Patent: Dec. 11, 2012

(54) PROCESS FOR PREPARING DIPHENYLMETHANEDIAMINE

(75) Inventors: Veronika Wloka, Mannheim (DE); Torsten Mattke, Freinsheim (DE); Daniel Breuninger, Bobenheim-Roxheim (DE); Markus Siegert, Heidelberg (DE)

(73) Assignee: BASF SE, Ludwigshafen (DE)

( * ) Notice: Subject to any disclaimer, the term of this patent is extended or adjusted under 35 U.S.C. 154(b) by 608 days.

(21) Appl. No.: 12/521,873

(22) PCT Filed: Jan. 2, 2008

(86) PCT No.: PCT/EP2008/050002
§ 371 (c)(1),
(2), (4) Date: Sep. 28, 2009

(87) PCT Pub. No.: WO2008/083997
PCT Pub. Date: Jul. 17, 2008

(65) Prior Publication Data
US 2010/0105951 A1    Apr. 29, 2010

(30) Foreign Application Priority Data
Jan. 8, 2007   (EP) .................................. 07100242

(51) Int. Cl.
*C09B 11/02*   (2006.01)

(52) U.S. Cl. ....................................................... 564/323

(58) Field of Classification Search .................. None
See application file for complete search history.

(56) References Cited

U.S. PATENT DOCUMENTS

| | | | |
|---|---|---|---|
| 2,781,245 A * | 2/1957 | Robertson et al. | ............ 423/357 |
| 6,433,219 B1 | 8/2002 | Strofer et al. | |
| 2007/0010692 A1 | 1/2007 | Steinbrenner et al. | |

FOREIGN PATENT DOCUMENTS

| | | | |
|---|---|---|---|
| DE | 1 901 993 | | 8/1970 |
| DE | 1 913 473 | | 9/1970 |
| EP | 0 570 799 | | 11/1993 |
| GB | 1192121 | * | 5/1970 |
| WO | 99 40059 | | 8/1999 |
| WO | 99 54289 | | 10/1999 |
| WO | 01 58847 | | 8/2001 |
| WO | 2005 007613 | | 1/2005 |

\* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

The invention provides a process for preparing diphenylmethanediamine, comprising the steps of
a) reacting aniline with formaldehyde in the presence of an acid,
b) neutralizing the acid with ammonia,
c) separating the reaction mixture from step b) into an aqueous phase and an organic phase,
d) treating the aqueous phase obtained in step c) with an oxide or hydroxide of an alkaline earth metal,
e) separating off the ammonia obtained in step d).

9 Claims, No Drawings

PROCESS FOR PREPARING DIPHENYLMETHANEDIAMINE

The preparation of diphenylmethanediamine (MDA) by reaction of aniline with formaldehyde in the presence of an acid is known and has been widely described. In practice the diphenylmethanediamine prepared in this way is always obtained as a mixture with more highly condensed polyphenylenepolymethylenepolyamines. Below, MDA is understood to refer to the mixture of dinuclear diphenylmethanediamine and more highly condensed polyphenylenepolymethylenepolyamines.

In the industry, the MDA is mostly converted by reaction with phosgene into diphenylmethane diisocyanate MDI.

For certain applications, for instance as a crosslinker in plastics or coatings, pure 2-nucleus MDA can also be used.

In the industry the MDA is prepared, as described, by reacting aniline with formaldehyde in the presence of an acid. The acid used is typically hydrochloric acid. Processes of this kind are general knowledge and are described for example in Kunststoffhandbuch, volume 7, Polyurethane, Carl Hanser Verlag, Munich, Vienna, 3rd edition, 1993, pages 76 to 86, and also in a large number of patent applications, WO 99/40059 being one example.

By varying the ratio of acid to aniline and of formaldehyde to aniline it is possible to adjust the fraction of the 2-nucleus product in the MDA in accordance with the particular requirement.

One problem associated with the preparation of MDA is the neutralization. On the one hand, the customary neutralization using aqueous sodium hydroxide solution is expensive. On the other hand, the brine produced in the procedure must be disposed of, expensively, as wastewater.

One possibility for overcoming these difficulties is the use of heterogeneous acidic catalysts. Thus WO 01/58847 describes a process for preparing MDA in which aniline is reacted with formaldehyde at a molar ratio of 1.7 to 100 in the presence of solid, inorganic, acidic catalysts. Disadvantages of the process described there are the inadequate service life of the catalyst, as a result of deactivation caused by fouling with oligomers; the titration of the acid groups of the catalyst with secondary amines present in the aniline or formed during the reaction, such as N-methyl amines; and the high costs of the catalyst and of downtimes resulting from the changeover and regeneration of the catalyst.

WO 2005/007613 describes a process for preparing MDA wherein the acidic catalyst is removed by an adsorbent. Through regeneration, the acid can be recovered from the adsorbent and used again. A disadvantage with this process too is the short service life of the adsorbent, a consequence of the surface fouling.

The use of oxides and/or hydroxides of other metals, particularly alkaline earth metals, for the purpose of neutralizing the reaction mixture has generally failed on account of the increased accompanying formation of solids, which can lead to plant disruptions.

It was an object of the present invention to develop a process for preparing MDA wherein simple, inexpensive, and operationally reliable separation of the acidic catalyst is possible without disadvantages for the process regime.

It has been possible to achieve this object, surprisingly, by using, as the neutralizing agent, ammonia which is recovered in a further process step by treatment with the oxide or hydroxide of an alkaline earth metal.

The invention accordingly provides a process for preparing diphenylmethanediamine, comprising the steps of a) reacting aniline with formaldehyde in the presence of an acid,
b) neutralizing the acid with ammonia,
c) separating the reaction mixture from step b) into an aqueous phase and an organic phase,
d) treating the aqueous phase obtained in step c) with an oxide or hydroxide of an alkaline earth metal,
e) separating off the ammonia obtained in step d).

The acid used is preferably a mineral acid, more particularly hydrochloric acid.

In principle it is possible in step d) to use oxides or hydroxides of the alkaline earth metals. Preference is given to calcium oxide and/or calcium hydroxide, on account of their ready availability and the largely trouble-free handling and disposal of the resultant byproducts.

The preparation of MDA in step a) takes place, as described above, by reaction of aniline with formaldehyde in the presence of acids as catalysts. Processes of this kind are general knowledge and are described for example in Kunststoffhandbuch, volume 7, Polyurethane, Carl Hanser Verlag, Munich, Vienna, 3rd edition, 1993, pages 76 to 86, and also in a large number of patent applications, WO 99/40059 being one example.

In place of or in a mixture with formaldehyde it is also possible to use at least one formaldehyde donor compound. The formaldehyde is used more particularly in the form of aqueous formalin solution, alcoholic formalin solution, hemiacetal, methyleneimine of a primary amine or N,N'-methylenediamine of a primary or secondary amine, and also para-formaldehyde.

The process of the invention can be implemented continuously, semicontinuously or batchwise, preferably continuously or semicontinuously.

In the case of the continuous procedure the reactants are metered in the desired proportion to one another into a reactor and a quantity of reaction product equal to the incoming stream is removed from that reactor. Examples of reactors used are tube reactors. In the case of the batchwise or semi-continuous procedure, the reactants are metered into a batch reactor, provided preferably with a stirrer and/or a pumped circulation, and the fully reacted reaction product is removed from the reactor and passed on for working up.

The process of the invention is implemented preferably with a molar ratio of aniline to formaldehyde of more than 2. The molar ratio of acid to aniline is preferably greater than 0.05. With these ratios there is increased formation of the respective two-nucleus products in the reaction mixture.

The reaction is implemented preferably at a temperature in the range between 0 and 200° C., preferably between 20 and 150° C., and in particular between 40 and 120° C. It has been found that as the temperature goes up there is an increase in the fraction of 2,2'- and 2,4'-isomers in the reaction product.

The pressure during the reaction is 0.1-50, preferably 1-10 bar absolute.

In the case of the batchwise and semicontinuous implementation of the reaction it is possible, after having metered in all of the reactants, to subject the reaction mixture to so-called aging. For that purpose the reaction mixture is left in the reactor or conveyed into another reactor, preferably a stirred reactor. The temperature of the reaction mixture at this stage is preferably above 75° C., more particularly within a range between 110 and 150° C.

The preparation in step a) is followed by the neutralization b) of the reaction mixture. For this purpose, ammonia is added to the reaction mixture. The ammonia may be supplied to the reaction mixture in gaseous form, saturated if appropriate with water; in the form of an aqueous ammonia solution; or in the form of a mixture of both phases. The combining of the ammonia and the reaction mixture takes place typically in a suitable mixing apparatus such as a stirred tank, a tube, with or without static mixing elements, or other apparatus. The addition of basic ammonia produces neutralization of the reaction mixture and, as a result, the formation of two, immiscible phases, the aqueous phase and the organic phase. Neutralization takes place at an average temperature of 40 to 120° C. under a pressure of 1 to 10 bar absolute.

The mixture from step b) is present, as described, in an organic phase and an aqueous phase. In step c) these phases are separated. The phases can be separated from one another by means for example of decanting. Thereafter the respective phases are worked up separately.

The aqueous phase, which is composed essentially of water, the ammonium salt of the catalyst acid, in solution in the water, and also traces of the aniline and formaldehyde reactants and of the MDA end product, is treated in step d) with the oxide and/or hydroxide of an alkaline earth metal. As described above, it is preferred to employ the corresponding compounds of calcium, generally in the form of milk of lime or slaked lime. The ammonium salt is decomposed, with formation of ammonia. This process step is known as a component step from the Solvay process for the production of sodium carbonate. The ammonia is separated off preferably by distillation or by stripping with steam or an inert gas.

If appropriate, the ammonia-rich gas phase is concentrated and purified in further steps, such as drying by adsorption or removal of steam by condensation, and can then be passed on again to the neutralization b).

In one particular embodiment the steam-comprising gas is passed over calcium oxide, also referred to as burnt lime. This procedure both dries the gas and converts the burnt lime into calcium hydroxide, known as slaked lime, which is supplied in turn to the ammonium salt decomposition in step d).

The low-ammonia liquid phase that remains after the ammonia has been removed can be disposed of as wastewater, if appropriate following further concentration or purification.

The organic phase separated off in step c), composed predominantly of MDA with residues of water, ammonia, and the products used for the preparation of the MDA, is likewise worked up. This is accomplished by means for example of single or repeated washing with water or, preferably, by multiple distillation for the purpose of removing, for example, aniline and water.

The MDA prepared by the process of the invention is typically reacted with phosgene to give MDI. Processes of this kind are general knowledge and have been widely described, as for example in the Kunststoffhandbuch, volume 7, Polyurethane, Carl Hanser Verlag, Munich, Vienna, 3rd edition, 1993, pages 76 to 86, and also in a large number of patent applications, of which WO 99/40059 or WO 99/54289 is one example.

For that purpose, customarily, the MDA and, if appropriate, the phosgene is or are dissolved in an inert solvent and brought to reaction. Solvents used are preferably inert organic solvents, particularly aromatic solvents, such as toluene or halogenated aromatic compounds, such as monochlorobenzene.

The stated process can be carried out in customary reactors, examples being stirred tanks, stirred tank cascades, columns and/or tube reactors, at known temperatures of, for example, 50 to 150° C., preferably 70 to 120° C., more preferably 70 to 100° C., under a pressure of 0.5 to 10 bar, preferably 0.8 to 5 bar, more preferably 0.8 to 1.5 bar, in one or more stages.

By way of example it is possible to carry out the phosgenation by a two-stage reaction in the presence of at least one inert organic solvent, the first phosgenating stage being implemented in a static mixer and the second phosgenating stage being implemented in a residence time apparatus.

The crude MDI prepared by the phosgenation can be purified by means of customary techniques, distillation for example. With preference it is possible, in a first purifying operation, to remove phosgene and, if appropriate, solvent, preferably substantially, more preferably completely, from the phosgenation reaction mixture, i.e., the crude MDI.

With preference it is possible subsequently to separate off desired monomeric MDI, such as 2,2'-, 2,4'- and/or 4,4'-MDI and/or mixtures comprising at least two of these isomers, by means of a suitable technique, preferably by means of distillation, at for example pressures of 2 to 50 mbar, preferably 2 to 20 mbar, and temperatures of 150 to 250° C., preferably 180 to 230° C., and/or preferably by means of crystallization, fractional crystallization for example.

In one particular embodiment of the process for preparing MDI it is possible to separate off the two-nucleus product from the crude MDA and to react it by means of gas phase phosgenation, as EP 570 799 describes, for example, to give two-nucleus MDI.

The MDI prepared in this way can in particular be reacted with compounds having at least two active hydrogen atoms to give polyurethanes.

The process of the invention permits the cost-effective and operationally reliable workup of MDA. There is no damage to the MDA. The ammonia used can be separated fully from the reaction product. The circulation of the ammonia avoids product losses. The aqueous salt solutions that arise can be disposed of without problems.

The purpose of the example below is to illustrate the invention.

EXAMPLE

In a laboratory apparatus with stirrer mechanism, 1 kg of aniline was mixed with 0.5 kg of 30% strength by weight hydrochloric acid and the mixture was heated to 50° C. Continuously over the course of an hour a total of 0.4 kg of a 40% strength by weight aqueous formaldehyde solution was metered in. Thereafter the mixture was heated to 100° C. and stirred at that temperature for 12 hours. During this time the aniline underwent reaction with the formaldehyde to give MDA.

After that about 350 g of 20% strength by weight ammonia solution at 50° C. was metered into the mixture, which was stirred intensely for 30 minutes. The stirrer was then switched off. The reaction mixture was separated into an organic phase and an aqueous phase. After phase separation had taken place, the phases were withdrawn separately from the laboratory apparatus.

The aqueous phase withdrawn comprised about 18.5% by weight of ammonium chloride.

1 kg of the aqueous phase was admixed in a temperature-conditioned laboratory apparatus with 150 g of calcium hydroxide (slaked lime). The resultant hydrous gaseous ammonia was passed through a drying tower filled with calcium oxide and in that way was dried. The dried ammonia was used again for the neutralization.

Following complete degassing, there remained in the apparatus an aqueous calcium chloride solution with a strength of approximately 20%, for disposal.

The invention claimed is:

1. A process for preparing diphenylmethanediamine, comprising:

reacting aniline with formaldehyde in the presence of an acid in an aqueous medium to form a reaction product comprising diphenylmethanediamine, water and the acid;

neutralizing the acid in the reaction product by mixing ammonia with the reaction product to form a neutralized product;

separating the neutralized product into an aqueous phase and an organic phase;

first contacting the aqueous phase with at least one of an alkaline earth metal oxide and an alkaline earth metal hydroxide to form ammonia gas; then second contacting the ammonia gas with the alkaline earth metal oxide to dry the ammonia gas and to form the alkaline earth metal hydroxide;

returning the ammonia gas to the reacting step; and returning the alkaline earth metal hydroxide formed in the first contacting step to the second contacting step.

2. The process according to claim 1, wherein the acid is hydrochloric acid.

3. The process according to claim 1, wherein the alkaline earth metal oxide is calcium oxide and the alkaline earth metal hydroxide is calcium hydroxide.

4. The process according to claim 1, further comprising:

reacting the diphenylmethanediamine formed by the reacting with phosgene to form diphenylmethane diisocyanate.

5. The processing according to claim 1, wherein the ammonia is returned to the reacting step in gaseous form.

6. The process according to claim 1, wherein the first contacting is carried out in one apparatus.

7. The process according to claim 1, wherein the ammonia formed by the first contacting is contacted with the alkaline earth metal oxide in a drying tower in the second contacting step.

8. The process according to claim 1, wherein the reacting step forms ammonium chloride.

9. The process according to claim 1, wherein the aqueous phase formed by the separating step consists of water, ammonium chloride and, optionally, one or more of ammonia, diphenylmethanediamine, aniline and formaldehyde.

* * * * *